(12) United States Patent
Gseller

(10) Patent No.: US 6,465,770 B2
(45) Date of Patent: Oct. 15, 2002

(54) DEVICE FOR POSITIONING OBJECTS

(75) Inventor: Rolf Gseller, Kirchheim/Teck (DE)

(73) Assignee: Leuze Electronic GmbH & Co., Owen/Teck (DE)

(*) Notice: Subject to any disclaimer, the term of this patent is extended or adjusted under 35 U.S.C. 154(b) by 0 days.

(21) Appl. No.: 09/824,535

(22) Filed: Apr. 4, 2001

(65) Prior Publication Data

US 2002/0017602 A1 Feb. 14, 2002

(30) Foreign Application Priority Data

Apr. 11, 2000 (DE) ............................................ 100 17 718

(51) Int. Cl.⁷ ................................................ H01J 40/14

(52) U.S. Cl. ........................... 250/221; 250/566; 422/65

(58) Field of Search ............................. 250/221, 223 R, 250/566; 422/63–65, 68.1; 356/39, 40

(56) References Cited

U.S. PATENT DOCUMENTS 5,439,645 A * 8/1995 Saralegui et al. ........... 366/128

* cited by examiner

*Primary Examiner*—Que T. Le
(74) *Attorney, Agent, or Firm*—Venable; Robert Kinberg

(57) ABSTRACT

A device for positioning objects in a desired position includes a transmitter for emitting light rays (11), a receiver for receiving light rays and an optical sensor (10) with an evaluation unit. The desired position is scanned with the transmitted light rays (11). The device additionally includes at least one holding device, in which a predetermined number of objects are stored in predetermined slide-in positions. Each slide-in position has a position mark associated therewith. The device furthermore includes a transport system for moving the holding device relative to the optical sensor. The holding device is stopped as soon as a position mark for a slide-in position of a predetermined object is detected by the optical sensor, wherein the predetermined object can be identified with the optical sensor through object marks located on the object.

25 Claims, 3 Drawing Sheets

DEVICE FOR POSITIONING OBJECTS

BACKGROUND OF THE INVENTION

The invention relates to a device for positioning objects in a desired position.

Devices of this type are generally used in installations with transport systems, for which the objects must be in predetermined desired positions for intake, so that they can be processed manually or by a machine.

One fundamental problem with these arrangements is that objects not only must be positioned with the highest possible precision in the predetermined desirable positions, but that the objects must also be clearly identifiable to avoid confusing the objects.

Examples of this are machines used to perform analyses of blood samples. The blood samples are contained inside individual sample tubes, which are supplied successively to the blood-analysis machine. A sample is typically removed from the tube inside by inserting a needle through the seal on the sample tube and is then analyzed.

Blood-analysis machines of this type have a high rate of throughput, so that a large number of sample tubes per time unit are supplied to the machine. One critical requirement for performing the analyses is that the individual sample tubes are clearly identifiable and the analyses can be assigned to the respective sample tubes. Confusing the individual samples could lead to a misdiagnosis for the patient from whom the blood sample was taken and could ultimately endanger the patient.

To avoid risks of this type, sample tubes are typically provided with unambiguous markings that can be identified by the operating personnel when performing the blood analysis. To be sure, confusing of the individual blood sample tubes can be avoided in this way. However, performing the blood analyses and, in particular, the transport of the sample tubes to the blood-analysis machine must be monitored by operating personnel. Apart from the fact that human error can still result in mistakes when assigning completed analyses to the associated samples in the sample tubes, plants of this type require a high number of personnel.

SUMMARY OF THE INVENTION

It is therefore the object of the invention to provide a device that ensures an exact, automatic positioning of objects, wherein a clear identification and tracking of the objects is simultaneously ensured as well.

The device according to the invention for positioning objects in a desired position achieves the above object with an optical sensor, comprising a transmitter for emitting light rays, a receiver for receiving light rays and an evaluation unit. The desired position is scanned with the aid of the transmitted light rays. The device is provided with at least one holding device in which a predetermined number of objects are stored in predetermined slide-in positions. Each slide-in position is characterized with a position mark. The device furthermore comprises a transport system for moving the holding device relative to the optical sensor. The holding device is stopped as soon as the position mark of a slide-in position for a predetermined object is detected by the optical sensor, wherein the respective object can be identified by the sensor through object marks.

The fundamental advantage of the device according to the invention is that the object not only can be positioned precisely in a desired position by the optical sensor, but the optical sensor also ensures an unambiguous identification of the objects. At the same time, the objects are also clearly assigned to the slide-in positions in the holding device.

As a result of the identification of the objects, a confusing of the objects is prevented with high certainty. In addition and owing to the clear assignment of the objects to the slide-in positions in the holding device, an exact localization and tracking of the individual objects within the conveying system is possible as well.

One particularly advantageous embodiment of the invention provides that the device is a component of an arrangement for analyzing blood. The arrangement comprises a blood-analysis machine, of which one component is a sample-taking device with needle. The objects are sample tubes, closed off with a seal, which contain blood samples. To remove samples from the sample tubes, the needle is inserted through the seal into the inside of the respective sample tube.

According to the invention, the sample tubes are supplied automatically to the needle, wherein the individual sample tubes are supplied successively to the sample-taking device, in sample holders that form holding devices. The sample tubes are inserted into slide-in positions in the sample holders.

Respectively one position mark is arranged on these slide-in units, which consists of a position barcode and two reference line elements. The number of the slide-in unit and thus its position within the conveying system is encoded in the position barcode. In addition, an object mark designed as object barcode is respectively arranged on the sample tubes.

The reference line elements form a target mark, which serves to position a slide-in unit in the desired position, in which the needle is arranged. The scanning range for the optical sensor during the positioning in the desired position is advantageously selected such that only the position marks at the slide-in units are detected, but not the object marks.

As soon as a slide-in unit has been positioned completely in the desired position, the slide-in unit position is determined in the device through detection of the position barcode. Following this, the scanning range of the optical sensor is increased, so that the object barcode is also detected. Not only is it possible to clearly identify the sample tubes and their content in the process, but also the assignment to the respective position barcode. Thus, an unambiguous localization of the sample tube within the transport system is ensured as well.

Once the slide-in unit is in the desired position, the needle of the sample-taking device is inserted into the respective sample tube and a sample is removed from the sample tube for performing an analysis. The analysis results are stored together with the information contained in the associated position barcode and the object barcode, so that the analysis result can be assigned clearly.

The transport of the sample tubes to the sample-taking device, as well as the removal of a sample from the sample tube all occur automatically and without use of personnel.

BRIEF DESCRIPTION OF THE DRAWINGS

The invention is explained in the following with the aid of the drawings, in which.

DETAILED DESCRIPTION OF THE INVENTION

Figure 1:
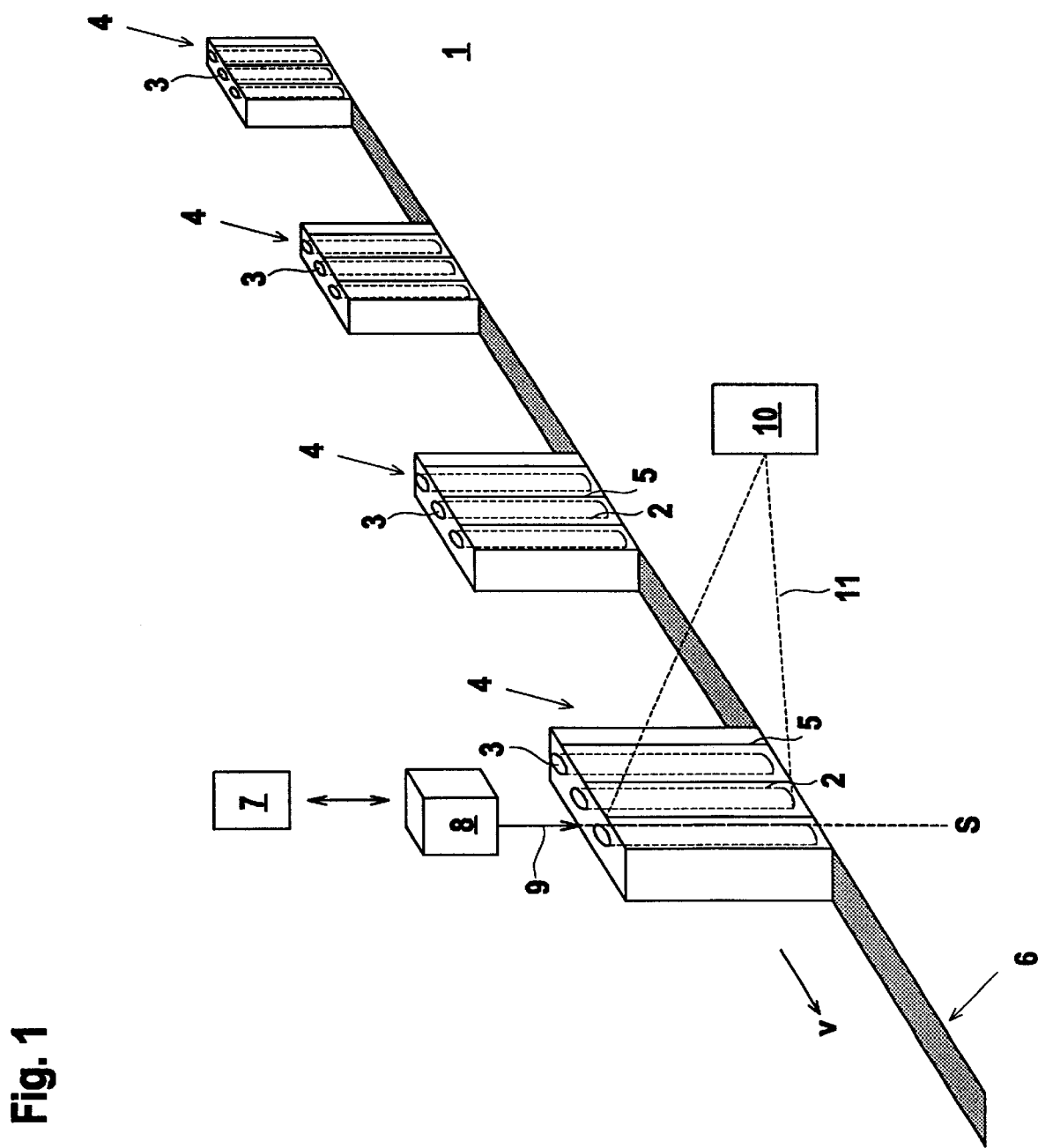
FIG. 1 shows a schematic representation of an exemplary embodiment of the device according to the invention, comprising sample holders as holding devices that are conveyed on a transport system and an optical sensor for positioning sample tubes forming the objects, which are positioned in a desired position inside sample-holder slide-in units.

FIG. 1 schematically shows an exemplary embodiment of the device according to the invention for positioning objects in a desired position.

In the present case, the device forms a component of an arrangement 1 for analyzing blood. The objects are sample tubes 2, preferably containing blood samples, which are respectively sealed on the top with a seal 3 in the form of a cork. The sample tubes 2 are stored in several sample holders 4 that form holding devices for the objects. The individual sample holders 4 have identical designs and respectively contain a predetermined number of slide-in units 5. The slide-in units 5 are also identical and hold respectively one sample tube 2.

The sample holders 4 are moved by means of a transport system 6 in a conveying direction v and are supplied to a blood-analysis machine 7. The blood-analysis machine 7 forms the core of an arrangement 1 for analyzing blood and is used to analyze blood samples.

The transport system 6 is a conveying system in which the sample holders 4 are arranged with predetermined spacing, one behind the other. The sample tubes 2 are positioned upright inside the respective sample holder 4. The sample tubes 2 are arranged with vertically extending longitudinal axes inside the sample holders 4, such that the seals on the tops of sample tubes 2 are freely accessible.

The sample holders 4 transported on the conveying system are supplied successively to a sample-taking device 8 that operates jointly with the blood-analysis machine 7. The sample-taking device 8 preferably forms a component of the blood-analysis machine 7.

The sample-taking device 8 is provided with an automatically controlled needle 9 for removing samples from the sample tubes 2. To remove a sample, the respective sample tube 2 is positioned in a desired position directly underneath the needle 9. The desired position in this case is a perpendicularly extending straight line S, which extends transverse to the conveying direction v of the conveying system. The longitudinal axis of needle 9 in this case extends along this straight line S.

As soon as a predetermined sample tube 2 is in the desired position, the conveying system is halted and the needle 9 is inserted through the seal 3 to remove a sample from the inside of sample tube 2.

The device for positioning the sample tubes 2 in the desired position essentially comprises an optical sensor 10 as well as a control unit, not shown herein, for actuating the optical sensor 10 and the sample-taking device 8.

The optical sensor 10 is designed as barcode reader, comprising a transmitter for emitting light rays 11, a receiver for receiving light rays, a deflection unit and an evaluation unit.

The transmitted light rays 11, which are guided over the deflection unit, periodically scan a scanning range. The barcode reader detects marks having contrast patterns, which are positioned inside the scanning range. In the process, an amplitude modulation is impressed upon the transmitted light rays 11 that are reflected on the marks, in accordance with the contrast pattern for the mark. The amplitude modulation is evaluated in the evaluation unit for detecting the mark.

The scanning range detected by the transmitted light rays 11 extends along the straight line S that forms the desired position. In principle, a scanning range in the shape of a line can be detected with the light rays 11 that are transmitted by the barcode reader. In the present case, a flat grid is scanned with the transmitted light rays 11 to detect marks arranged on the sample holder 4 and/or the sample tubes 2. The grid forms a rectangular flat element, wherein the size of this flat element in the plane for the scanned sample holder 4 is adapted to the dimensions of the marks to be detected.

The grids scanned by the transmitted light rays 11 and the marks to be detected are shown in FIGS. 2–5.

FIGS. 2–5 respectively show the side surface of a sample holder 4, which is facing the optical sensor 10 and is scanned by the transmitted light rays 11.

The sample holder 4 essentially has a cube-shaped contour, wherein the side surface that is facing the optical sensor 10 basically forms a flat, rectangular surface. The sample holder 4 shown in FIGS. 2–5 contains five identical slide-in units 5 extending in the vertical direction. The slide-in units 5 are arranged equidistant and open on the top of sample holder 4. The seals of the essentially cylindrical sample tubes 2, positioned in the slide-in units 5, project over the upper edges of the slide-in units 5.

Position marks are affixed to the undersides of the slide-in units 5, on the side surface of the sample holder 4, to position a slide-in unit 5 in the desired position. Each position mark assigned to a slide-in unit 5 extends in the direction of the longitudinal axis of this slide-in unit 5.

Each position mark has a position barcode 12. Encoded in this position barcode 12 is the number of the respective slide-in unit 5 of sample holder 4, wherein the slide-in units 5 of all sample holders 4 are provided with consecutive numbers. Thus, the position of each slide-in unit 5 within the complete set of all sample holders 4 of the transport system 6 is clearly characterized by the respective number. It is advantageous if the number for a slide-in unit 5 is not only contained in the respective position barcode 12 on the slide-in unit 5, but is also affixed in clear text in the form of a number sequence. The position barcodes 12 are composed of a series of light and dark line elements, the longitudinal axes of which extend transverse to the longitudinal axis of the respective slide-in unit 5 and transverse to the scanning direction of the light rays 11 transmitted by the optical sensor 10.

Each position barcode 12 is provided with a rest zone of a predetermined width at its longitudinal ends. A reference line element 13 is positioned in each of these rest zones. The longitudinal axes for the reference line elements 13 extend parallel to the longitudinal axes of the line elements for the respective position barcode 12.

The reference line elements 13 forming a target mark constitute a component of a position mark and serve to position the respective slide-in unit 5 in the desired position.

An object barcode 14 or object mark is respectively affixed to the outside of a sample tube 2 and contains the encoded content of a sample tube 2.

Each slide-in unit 5 has an opening 15 in the side surface of sample holder 4, which surface is facing the optical sensor 10. The opening 15 is adapted to the size of an object barcode 14, so that this barcode is clearly and completely visible through the opening 15 and can be detected by the optical sensor 10, provided the sample tube 2 is positioned inside the slide-in unit 5. For this, the longitudinal axis of the opening 15 extends in longitudinal direction of the slide-in unit 5.

A reference barcode 16 for checking whether the slide-in unit 5 contains a sample tube 2 is furthermore provided on the inside that is positioned opposite the opening 15 of each slide-in unit 5. The reference barcode 16 is visible through the opening 15 if the slide-in unit 5 is empty and thus can be scanned by the optical sensor 10. However, if a sample tube 2 is positioned inside the slide-in unit, the sample tube 2 covers the reference barcode 16, thus preventing the barcode from being scanned by the optical sensor 10.

The optical sensor 10 scans the position barcode 12 or marks, the object barcode 14 or marks and the reference marks 16, when the scanning range of the sensor 10, which is a flat grid with a longitudinal axis extending along straight line S, senses the desired position. The needle 9 of the sample-taking device 8 also extends along this straight line.

The grid width is constant and is given the reference $\Delta d$ in FIGS. 2–5. The optical sensor 10 can be switched between two different operating modes. In a first operating mode for positioning a slide-in unit 5 in the desired position, a grid having the width $\Delta d$ and the length $\Delta x$ is scanned with light rays 11 transmitted by the optical sensor 10. The grid length is adapted to the position barcode 12 or marks, such that the position marks are completely detected by the optical sensor 10 while the object barcode 14 or marks and the reference barcodes 16 are outside of this grid and are undetected in the first operating mode.

In a second operating mode for a slide-in unit 5 in the desired position, the optical sensor 10 scans a grid with width $\Delta d$ and length $\Delta y$. The grid length $\Delta y$ in this case extends over the complete height of the sample holder 4, so that in the second operating mode, the position barcode 12 or marks as well as the object barcode 14 or marks and the reference barcodes 16 are detected.

The switch from the first to the second operating mode occurs via a trigger signal that is generated internally in the evaluation unit as soon as the optical sensor 10 detects that a slide-in unit 5 is in the desired position.

The switch from the second to the first operating mode occurs via an external trigger signal, which is preferably generated inside the control unit and read into the optical sensor 10.

The operation of the device according to the invention is explained in the following with the aid of FIGS. 2–5.

Figure 2:
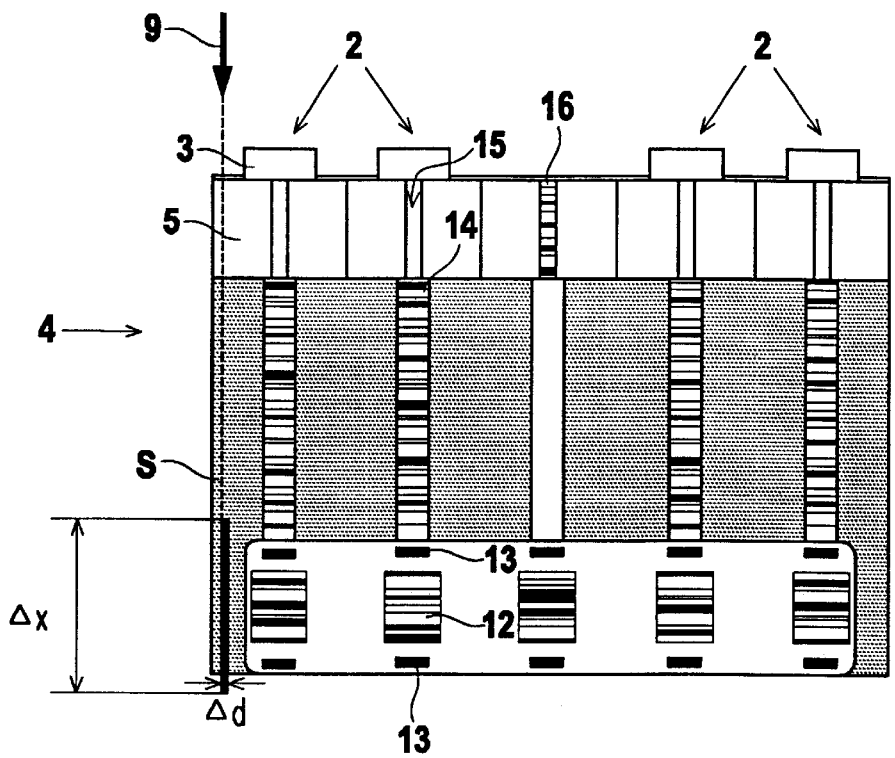
FIG. 2 is a view from the side of a sample holder according to FIG. 1 with sample tubes stored in slide-in units and positioned outside of the desired position.

With the arrangement according to FIG. 2, the sample holder 4 is moved along the conveying direction v, relative to the optical sensor 10. For this example, none of the slide-in units 5 are in the desired position. The optical sensor 10 is in the first operating mode, so that a grid with length $\Delta x$ is scanned to detect the position marks.

The positioning in the desired position is completed once the grid rests completely on the reference line elements 13 of a position mark that form the target mark.

The identically designed reference line elements 13 in this case are somewhat longer than the width $\Delta d$ of the grid and shorter than the seal diameters. If it is determined during the scanning of a position barcode 12 or mark that the complete grid rests on the reference line elements, it ensures that the respective slide-in unit 5 is positioned with sufficient accuracy in the desired position. Thus, the needle 9 of the sample-taking device 8 is definitely positioned above the seal 3 and punctures this seal. In particular, the dimensioning of the grid and the reference line elements 13 ensures that a slide-in unit 5 is not tilted relative to the straight line S that forms the desired position, which would hinder the insertion of needle 9 into the seal 3.

Figure 3:
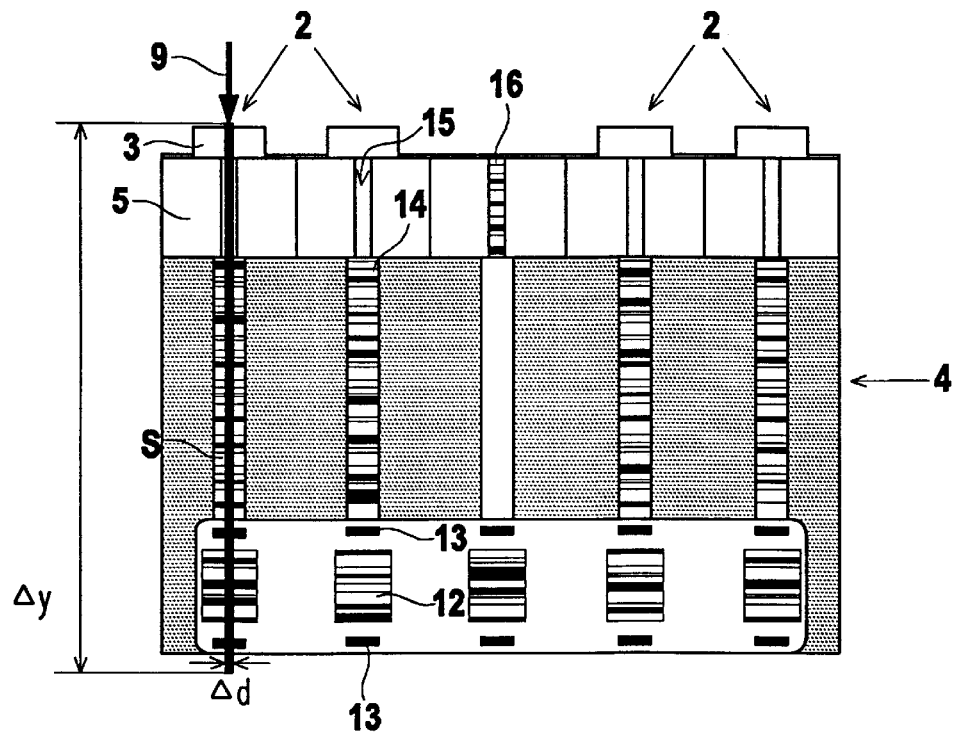
FIG. 3 shows a sample holder according to FIG. 2, with a slide-in unit containing a sample tube and positioned in the desired position.

After a slide-in unit 5 is positioned in the desired position and the position barcode 12 of the respective slide-in unit 5 is detected, the conveying system is halted and the optical sensor 10 switched to the second operating mode. The scanning range is then increased to the grid with length $\Delta y$ to detect the object barcode 14 of sample tube 2, which is positioned in the slide-in unit 5 in the desired position. This situation is shown in FIG. 3.

Following detection of the position mark for slide-in unit 5 in the desired position and the object mark of the respective sample tube 2, the needle 9 of sample-taking device 8 is inserted into the sample tube 2 with the aid of the control unit and through the seal 3. The sample taken in the process is analyzed in the blood-analysis machine 7. The analysis result is stored together with the previously determined position barcode 12 and the object barcode 14, so as to ensure that the analysis result is clearly assigned to the sample tube 2 and this tube is arranged inside the slide-in unit 5 of sample holder 4.

As soon as these operations are completed, the trigger signal for switching to the first operating mode is generated in the control unit. At the same time, the control unit again starts the movement of the conveying system. Following this, the sample holder 4 is moved until the next slide-in unit 5 is positioned in the desired position. In this way, all slide-in units 5 of sample holder 4 are successively positioned in the desired position.

Figure 4:
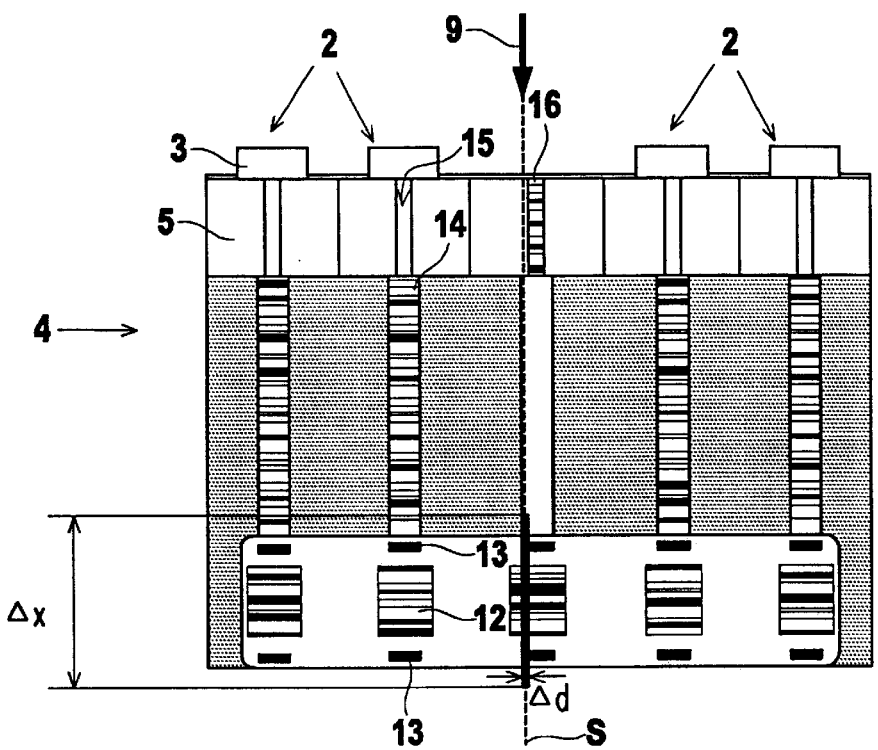
FIG. 4 shows a sample holder according to FIG. 2, with an empty slide-in unit positioned outside of the desired position.

FIG. 4 shows the positioning of an empty slide-in unit 5 in the desired position. The positioning is not completed since the grid for the optical sensor 10 does not yet rest completely on the reference line elements 13 of this slide-in unit 5.

Figure 5:
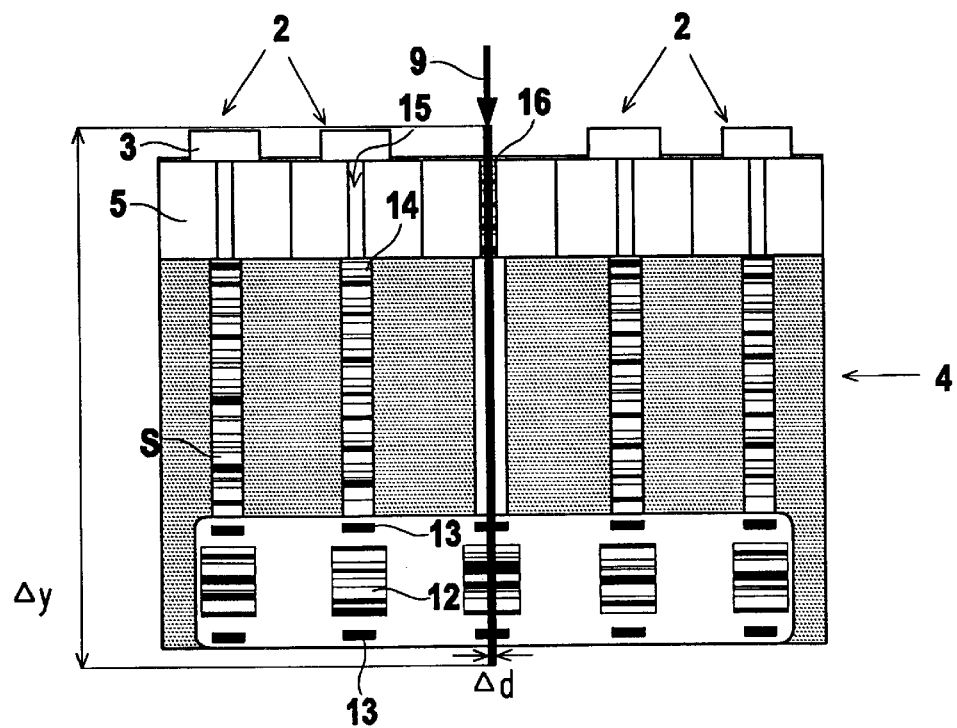
FIG. 5 shows a sample holder according to FIG. 2, with an empty slide-in unit positioned inside the desired position.

FIG. 5 shows the slide-in unit 5 in the desired position, wherein a switch to the second operating mode has already occurred following detection of the position barcode 12 at this slide-in unit 5. Since this slide-in unit 5 is empty, the reference barcode 16 and not an object barcode 14 of a sample tube 2 is detected at the slide-in unit 5. As a result, the evaluation unit for sensor 10 determines that the slide-in unit 5 is empty. In that case, a warning or error message is preferably generated in the evaluation unit, which indicates to the operating personnel that the slide-in unit is not occupied. Due to the warning or error message, the sample-taking device 8 is also deactivated via the control unit, thus keeping the needle 9 in the idle position to avoid damages or malfunctions.

What is claimed is:

1. A device for positioning objects in a desired position, each object having a machine readable mark thereon for identification of the object; said device comprising:
   an optical sensor including a transmitter for emitting light rays, a receiver for receiving light rays and an evaluation unit wherein the desired position of an object is scanned with the transmitted light rays;
   at least one holding device in which a number of the objects are stored in predetermined slide-in positions wherein a position mark indicates each slide-in position; and a transport system for moving said at least one holding device relative to the optical sensor in a conveying direction, wherein relative movement between the optical sensor and the holding device is stopped as soon as the position mark for a slide-in position of a predetermined object is detected by said optical sensor and wherein said optical sensor identifies the predetermined object through the machine readable mark.

2. A device according to claim 1, wherein said optical sensor is a barcode reader.

3. device according to claim 1, wherein said at least one holding device has slide-in units and is a sample holder, and wherein sample tubes form the objects and are stored in the slide-in units, which form the slide-in positions.

4. A device according to claim 3, wherein the sample tubes stored inside the slide-in units of the sample holder are arranged parallel and at a distance to each other, and the longitudinal axes of the sample tubes extend transverse to the conveying direction of the sample holder.

5. A device according to claim 4, wherein the desired position extends along a straight line S, which runs parallel to the longitudinal axes of the sample tubes stored inside the sample holder.

6. A device according to claim 5, wherein the transmitted light rays of optical sensor are guided along the straight line S that forms the desired position.

7. A device according to claim 6, wherein a rectangular, flat grid is scanned with the transmitted light rays, and the straight line S that defines the desired position extends inside this grid, in a longitudinal direction of the grid.

8. A device according to claim 3, wherein each position mark is respectively arranged in the longitudinal axis of the associated slide-in unit, on the side surface of sample holder that is facing the optical sensor, and wherein each position mark is respectively arranged in the region lower than a sample tube stored in the respective slide-in unit.

9. A device according to claim 8, wherein each position mark is provided with a position barcode that contains the encoded number for the slide-in unit.

10. A device according to claim 8, wherein each position mark has two reference line elements, arranged at a distance to each other and one behind the other in a longitudinal direction of the slide-in unit, the longitudinal axes of the reference line elements extending transverse to the longitudinal axis of slide-in unit.

11. A device according to claim 9, wherein each position mark has two reference line elements, the reference line elements being arranged on both sides of the position barcode in a rest zone.

12. A device according to claim 10, wherein the length of the reference lines elements is shorter than the width of the grid scanned by the optical sensor.

13. A device according to claim 12, wherein the reference line elements are designed to be identical.

14. A device according to claim 10, further comprising a needle for insertion into a seal of a sample tube wherein once the evaluation device of the optical sensor determines that a slide-in unit is positioned in the desired position via the scanning of its position mark, the needle can be inserted through the seal at the upper end of the sample tube for taking a sample from the sample tube stored inside the slide-in unit.

15. A device according to claim 14, wherein the diameter of the seal is larger than the length of the reference line elements.

16. A device according to claim 1, wherein the machine readable mark is an object barcode and the objects are sample tubes, each object barcode being affixed to the outside of a sample tube and containing the encoded content of sample tube.

17. A device according to claim 16, wherein each slide-in unit is provided with an opening on the side facing the optical sensor, through which the object barcode is visible on a sample tube that is stored inside this slide-in unit.

18. A device according to claim 17, further comprising a reference barcode for checking whether the slide-in unit contains a sample tube, the reference barcode being arranged opposite the opening on the inside of a slide-in unit, wherein the reference barcode is visible through the opening if the slide-in unit is empty and is covered by the sample tube if the slide-in unit is occupied.

19. A device according to claim 14, wherein, for determining the desired position of a slide-in unit, the optical sensor has means for scanning only the lower area of the sample holder in a first operating mode, and the optical sensor has means for scanning the entire height of the sample holder in a second operating mode when the slide-in unit is in the desired position.

20. A device according to claim 19, wherein a slide-in unit is in its desired position as soon as the complete width of the grid for the transmitted light rays is positioned on the reference line elements of the respective position mark.

21. A device according to claim 20, wherein the optical sensor further includes means for generating a trigger signal once the reference line elements of a position mark are detected completely, the trigger signal triggering a switch from the first to the second operating mode.

22. A device according to claim 20, wherein the sample holder is stopped if a slide-in unit is in the desired position in the first operating mode, so that following identification of the sample tube that is stored inside the slide-in unit in the second operating mode, the needle can be inserted into its seal for taking a sample.

23. A device according to claim 22, wherein each slide-in unit is provided with an opening on the side facing the optical sensor and further comprising a reference barcode for checking whether the slide-in unit contains a sample tube, the reference barcode is arranged opposite the opening on the inside of a slide-in unit, so that the reference barcode is visible through the opening if the slide-in unit is empty and is covered by the sample tube if the slide-in unit is occupied and means for generating an error or warning message if a reference barcode is detected in the second operating mode.

24. A device according to claim 21, further comprising means for generating an external trigger signal for switching to the first operating mode from the second operating mode, wherein the external trigger signal can be read into the optical sensor.

25. A device according to claim 14, wherein the device forms a component of an arrangement for analyzing blood.

* * * * *